(12) United States Patent
Batzdorff

(10) Patent No.: US 9,664,580 B2
(45) Date of Patent: May 30, 2017

(54) PRESSURE INDICATING LINER AND METHOD OF USE

(71) Applicant: OTTO BOCK HEALTHCARE GMBH, Duderstadt (DE)

(72) Inventor: Jonathan Batzdorff, Santa Rosa, CA (US)

( * ) Notice: Subject to any disclaimer, the term of this patent is extended or adjusted under 35 U.S.C. 154(b) by 257 days.

(21) Appl. No.: 14/383,202

(22) PCT Filed: Mar. 5, 2013

(86) PCT No.: PCT/US2013/029130
§ 371 (c)(1),
(2) Date: Sep. 5, 2014

(87) PCT Pub. No.: WO2013/134268
PCT Pub. Date: Sep. 12, 2013

(65) Prior Publication Data
US 2015/0052993 A1 Feb. 26, 2015

Related U.S. Application Data

(60) Provisional application No. 61/634,746, filed on Mar. 5, 2012.

(51) Int. Cl.
*G01L 19/08* (2006.01)
*A61F 2/76* (2006.01)
(Continued)

(52) U.S. Cl.
CPC ............ *G01L 19/08* (2013.01); *A61B 5/4851* (2013.01); *A61B 5/6811* (2013.01);
(Continued)

(58) Field of Classification Search
CPC .... A61B 2562/0247; A61B 2562/0266; A61B 5/4851; A61B 5/6811; A61B 5/6843;
(Continued)

(56) References Cited

U.S. PATENT DOCUMENTS 3,732,578 A * 5/1973 Pollack ................. A61F 2/7812
264/222
6,136,039 A * 10/2000 Kristinsson ........... A61F 2/7812
623/36
(Continued)

FOREIGN PATENT DOCUMENTS

JP 2009222511 A 10/2009
WO 2012167384 A1 12/2012

OTHER PUBLICATIONS

PCT International Search Report for PCT International Patent Application No. PCT/US2013/029130, mailed May 29, 2013.

*Primary Examiner* — Francis Gray
(74) *Attorney, Agent, or Firm* — Craig M. Stainbrook; Stainbrook & Stainbrook, LLP

(57) ABSTRACT

A sheet material, contoured sheet material, or interface liner which is formulated and fabricated such that, when pressure is applied to said sheet material, contoured sheet material, or interface liner, said sheet material, contoured sheet material, or interface liner indicates the spot at which the pressure has been applied by effecting a change in the color or appearance of said sheet material contoured sheet material, or interface liner itself.

15 Claims, 3 Drawing Sheets

(51) Int. Cl.
   *A61B 5/00*   (2006.01)
   *A61F 2/78*   (2006.01)
(52) U.S. Cl.
   CPC .............. *A61B 5/6843* (2013.01); *A61F 2/76* (2013.01); *A61F 2/7812* (2013.01); *A61B 2562/0247* (2013.01); *A61B 2562/0266* (2013.01); *A61F 2002/7635* (2013.01); *F04C 2270/0421* (2013.01)
(58) Field of Classification Search
   CPC .. A61F 2002/7635; A61F 2/76; A61F 2/7812; G01L 19/08
   See application file for complete search history.

(56) References Cited

U.S. PATENT DOCUMENTS

| | | | |
|---|---|---|---|
| 7,377,944 B2 | 5/2008 | Janusson et al. | |
| 7,780,741 B2 | 8/2010 | Janusson et al. | |
| 8,052,760 B2 | 11/2011 | Egilsson et al. | |
| 8,097,043 B2 | 1/2012 | Egilsson | |
| 2004/0006286 A1* | 1/2004 | Horton | A61B 5/1036 600/592 |
| 2004/0232742 A1 | 11/2004 | Oehler | |
| 2005/0047677 A1* | 3/2005 | Alaimo | A43B 1/0045 382/286 |
| 2006/0084036 A1* | 4/2006 | Boston | A61B 5/1078 433/215 |
| 2006/0111792 A1 | 5/2006 | Shannon | |
| 2007/0061017 A1 | 3/2007 | Wilson | |
| 2007/0080479 A1 | 4/2007 | Arbogast et al. | |
| 2009/0240344 A1 | 9/2009 | Colvin et al. | |
| 2013/0211259 A1* | 8/2013 | Komistek | G06F 19/3443 600/440 |
| 2015/0289999 A1* | 10/2015 | Radspieler | A61F 2/7812 623/34 |
| 2015/0297369 A1* | 10/2015 | Mosler | A61F 2/7812 623/36 |

\* cited by examiner

PRESSURE INDICATING LINER AND METHOD OF USE

BACKGROUND

An human limb prosthesis is typically custom made for each amputee by a prosthetist. The prosthesis consists of various functional components, such as a foot and knee, fastened to the amputee's body by way of a receptacle which accepts the amputee's residual limb. The receptacle is called a socket. The most critical aspect of a prosthesis is the fit of the socket. It must be comfortable and supportive. If the socket does not fit properly, the result can be pain, injury to the skin, poor function of the prosthesis or any combination of these problems. The socket is typically made from a mold or impression of the residual limb. The mold may be modified by the prosthetist to relieve potential pressure by the socket on boney or pressure sensitive areas. The mold is then used to make a diagnostic socket, also referred to as a test socket. The test socket is made of a clear rigid plastic material. The test socket is then attached to the functional components and the amputee can try the prosthesis. Both the amputee and the prosthetist use this test socket fitting as an opportunity to determine the existence of any problems in the fit of the socket. The amputee by report pain or the prosthetist may observe skin discoloration in the test socket due to improper or uneven pressures between the socket and the residual limb. When socket problems are identified, the test socket can be adjusted by heating and reforming a spot in the plastic socket or sanding an area in the plastic.

From U.S. Pat. No. 6,136,039 and US 2009/0240344 A1 a prosthetic liner is known that consists of two or more layers. These layers can be made from polymeric material, silicone or other elastomeric materials. These liners are supposed to increase the wearing comfort for the wearer when the liner is used to couple a prosthesis socket to an amputation limb.

From U.S. Pat. No. 7,377,944 B2 and U.S. Pat. No. 7,780,741 B2 it is known to use a prosthetic liner to hold a variety of different sensors to monitor the physiological health of the enclosed limb. The sensor can be included in the liner material or in a channel formed between an inner layer and an outer layer of the respective liner. The sensors can be for example temperature sensors, humidity sensors, sensors to measure blood pressure, glucose or body fat.

It is often very difficult to identify precisely where the improper pressures are for several reasons:
a) The amputee may feel discomfort but not be able to describe exactly where it is coming from in the prosthesis.
b) The amputee may have poor sensation and not be able to feel discomfort though pressures may exist that can cause damage to the skin. In this case the amputee cannot describe the origin of the pain in the prosthesis.
c) Usually the amputee wears a liner or interface between the skin and the socket for comfort or function. This interface prevents the prosthetist from observing the skin through the clear test socket.

An orthopaedic brace is properly called an orthosis. Many orthoses require a precise fit to the body surface of the user. For the same reasons as in the case of prosthetic fitting, assessing the fit of a brace can be challenging with the limited tools and materials available.

There are numerous other instances where it is important to assess the pressure against the skin such as in fitting wheelchair cushion, an arch support, or shoes.

SUMMARY

A material has been developed which changes color at the high pressure areas. The material has been used to make a prosthetic liner. The amputee can wear the liner in a test socket so that high pressures in the socket will appear as color changes in the liner. The resulting color change in the liner is observed through the clear test socket and allows the prosthetist to pinpoint precisely where any high pressure areas are and make the appropriate adjustments. The pressure indicating liner can be worn either directly against the skin or in conjunction with other interface materials. The liner can be used both as a diagnostic tool and can then function as a liner in the finished prosthesis.

The material can be used for the socket of a prosthesis, an orthopaedic appliance, a wheelchair, or for any application requiring analysis of body pressure against another surface or between two surfaces.

In one embodiment of the liner, the liner consists of 2 layers of elastomer, gel, or other appropriate material. The outer layer is a different color from the inner layer and when worn by the amputee in the clear test socket, said outer layer thins out under pressure thereby revealing the layer beneath it. The color difference can be observed by the prosthetist and appropriate adjustments can be made. Another embodiment uses only one layer of a material that changes color under pressure. Another embodiment uses only one layer which thins, allowing another interface material of a different color to show through at the high pressure area. In another embodiment the liner takes the form of a flat sheet which can be used to measure pressure in other applications requiring such as orthopaedic braces.

There are many previous patents for prosthetic liners such as 2009-240344, 2007-080479, 2006-111792, 2007-061017, 8097043, and 8052760, but not one of these liners is designed to indicate pressure within the socket and none utilize color in any functional way. Current liners have been used as shock absorbers skin protectors or as means for attaching the prosthesis to the body. No prior art involves a liner which is used to indicate socket pressures.

A new method involves the use of the sheet or liner, in any of its embodiments, as a pressure assessment tool for constructing and adjusting a prosthetic socket, orthopaedic device, or for any application requiring analysis of body pressure against an object.

In a preferred embodiment of the present invention the sheet material, contoured sheet material, or interface liner comprises at least a first layer and a second layer. The first layer is made from a partially translucent material. The second layer is made from a material that has a colour. Also the first layer may be coloured by for example pigmenting it, but in this case the two colours of the first layer and the second layer have to be different from one another. In a preferred embodiment, the colour of the first layer is lighter than the colour of the second layer. However, it is also possible to use a darker colour for the first layer than for the second layer.

If now a pressure is applied to the sheet material, contoured sheet material or the interface liner the first layer thins out under this pressure. Since the material of the first layer is partially translucent, the translucence and hence the visibility of the colour of the second layer through the first layer is depending on the thickness of the first layer. Hence, when the first layer thins out, the visibility changes. The brightness of the second colour that can be seen through the first layer is thus a measure for the thickness of the first layer and accordingly for the pressure applied.

In a preferred embodiment, the first layer has a thickness of 0.5 mm to 1.5 mm, in particular 1 mm.

Preferably, the first layer and the second layer have different durometer or hardness, wherein the second layer in particular has a larger durometer or hardness than the first layer. If a pressure is applied to the sheet material, the contoured sheet material or the interface liner, both the material of the first and the second layer are compressed. The amount of compression strongly depends on the hardness or the durometer of the material. Hence, a second layer made from a harder material than the first layer is less compressed and hence transfers the applied pressure into the first layer.

In a preferred embodiment the first layer and/or the second layer is made from silicone having a shore hardness of 30 to 35 shore 00. Of course it is possible, to make both, the first layer and the second layer from the same material with the same hardness or durometer.

In a preferred embodiment, the first layer thins out due to compression or displacement of the material of the first layer.

In a preferred embodiment at least one layer of the sheet material, contour sheet material, or interface liner is made from a viscoelastic material or a material having the ability to flow under the influence of pressure. These materials can for example be polyurethane or a TPE.

These materials have the advantage that the thinning of the liner due to the applied pressure is still visible after the limb and the liner have been removed from the socket. In this case it is not necessary to use a transparent material for the socket. If the viscoelastic material or the material being able to flow under the influence of pressure is used it is possible to use a one layer liner, which is hence made from only one layer consisting of one material. If this material is coloured it changes the colour in the compressed areas. Due to hysteresis effects or a permanent deformation of the elastomer material it is possible to analyze and estimate the distribution of pressure on the liner after removing the limb and the liner from the socket. Of course, it is also possible, to use these materials as an outer layer for a sheet material, contoured sheet material or interface liner consisting of more than one layer.

A method for the production of a liner as described here consists of the following steps according to the invention:
 a) The fabrication of a first partial liner using the casting, injection molding or dipping method.
 b) The fabrication of a second partial liner on the first partial liner using the casting, injection molding or dipping method.

The dipping methods can be carried out particularly economically, especially for copolymers. For the fabrication of liners made from silicon and polyurethane, molding or casting methods in particular can be used. Furthermore, appropriate injection molding methods are especially deployable for copolymers and spray-on silicon types. In this way for example, a material of the addition curing type with the designation Renew 20 can be used, which is available from the producer Renew Materials (http://www.renewmaterials.com/products/silicone20.php).

It is advantageous if the first partial liner is an inner liner and the second partial liner an outer liner. This means that the inner liner forms the second layer, while the second partial liner forms the first layer. The outer liner is thus made from the partially translucent material, which of course can be given a color in every embodiment, for example by means of appropriate pigmentation. In contrast to this, the inner liner is made from the colored material whose color should appear through the material of the outer liner.

A method according to the invention for the determination of pressure distribution of a pressure that is applied to a body part of a person, in particular an amputation stump, by an orthopedic appliance consists of the following steps:
 a) The arrangement of a sheet material, contoured sheet material, or interface liner on the body part.
 b) The positioning of the body part with the sheet material, contoured sheet material or interface liner in a transparent molding.

With a method such as this, it is possible to determine the pressure distribution which, for example, is exerted by an orthosis or a prosthesis on the respective body part of the wearer of the orthopedic appliance. To do this, a lubricant is preferably applied prior to the positioning of the body part in the molding, in order to reduce a sliding resistance between the sheet material, contoured sheet or interface liner and the molding. The lubricant can be a water-alcohol mixture or soap solution, for example. These have the advantage that they are washed and removed easily. A lubricant such as this is especially advantageous if the material that is thinned out by the pressure is thinned out by displacement. Alternatively, lubricant coatings can be applied, for example in the form of parylene. The lubricant can be applied to the molding and/or the sheet material, contoured sheet material or interface liner.

In all the named embodiments, the material of the first layer, which is thinned out, can be, for example, a foam material, such as a foam elastomer. Hence this material contains small air bubbles, which are compressed when pressure is applied. Thus the thinning out of this material does not occur by displacement, but by a compression of the material. In this case the sliding resistance against the molding is irrelevant to the operation. In particular for the case, that a viscoelastic material or a material with the ability to flow under the influence of pressure is used, no lubricant is necessary, since the thinning of the material occurs due to a compression of the respective material.

Since the molding is designed to be transparent, the color impression of the material in the molding can be well observed. By looking at the strength with which the color of the second layer appears through the first layer, the pressure distribution of the applied pressure can at least be qualitatively determined. In this way, it is possible to determine the optimal fit for orthoses and prostheses. It is advantageous if the molding is a prosthesis socket.

The sheet material, contoured sheet material, or interface liner can be used to indicate variations in pressure between the surfaces of two objects. It can also be used in a method, where it is used on a residual limb of an amputee and is then inserted into a clear or translucent plastic prosthetic socket so that changes in the appearance of said liner as a result of pressure variations can be observed through said prosthetic socket.

In a preferred method the sheet material, contoured sheet material or interface liner as described above is used on a portion of the surface of a human body which is then pressed on to a clear or translucent plastic shell so that changes in the appearance of said liner as a result of pressure variations can be observed through said plastic shell. As already mentioned, this plastic shell can be an orthosis or a prosthetic device.

SUMMARY

This is a material and sheet-like structure which allows one to visually note high or low pressure areas along a flat or curved surface by creating a change in appearance in the areas of higher pressure dynamically while the pressure is being applied. Various embodiments of the invention include versions with one layer and versions with multiple layers. The method and the result of the method is the use of the sheet or liner as a pressure assessment tool and a fitting tool for constructing and adjusting a prosthetic socket, orthopedic device, or for any application requiring analysis of body pressure against an object.

DETAILED DESCRIPTION

Figure 1:
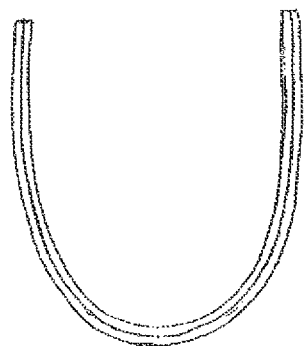
FIG. 1 is a cross sectional drawing of a two-layered liner in which the inner layer is a different colour than the outer layer and they are made of such a material that when pressure is applied, the inner surface shows through the outer surface when viewed from outside of the liner.

FIG. 1—The first embodiment is a thin two-layer flexible sheet-like material fabricated out of an elastomeric gel such a silicone, urethane, thermoplastic elastomer, or other suitable material. The layers are pigmented and fabricated in such a way that the outer gel becomes more transparent when pressure is applied so as to allow the inner layer to show through, indicating a high pressure area.

Figure 2:
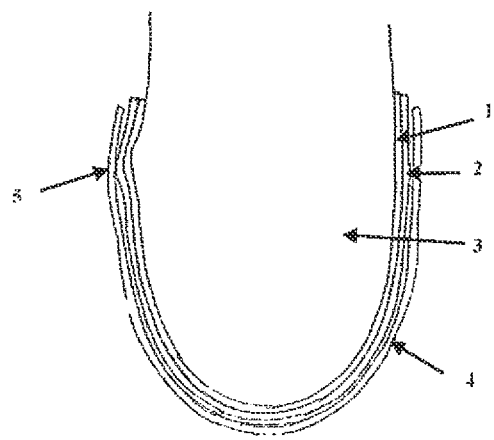
FIG. 2 is a cross sectional drawing of a residual limb with the FIG. 1 liner shown installed in a prosthetic socket. A high pressure area is indicated.

FIG. 2—In the first embodiment the liner is made of two layers of gel or other suitable material. The inner layer of the liner (1) is made of a different color than the outer layer of the liner (2). When the residual limb (3) is inserted into the liner, which is then inserted into the transparent or translucent socket (4), the outer layer thins out in the high pressure specific spot (5) allowing the different coloured inner layer to appear through the outer layer when viewed from outside of the socket. The change in colour indicates the areas of high pressure while the patient is wearing the device.

Figure 3:
FIG. 3 is a cross sectional drawing of a single-layered liner made of a material that changes colour when pressure is applied.

FIG. 3—The second embodiment is a flexible sheet-like material fabricated out of an elastomeric gel such as silicone, urethane, thermoplastic elastomer, or other suitable material. The gel is pigmented and fabricated in such a way that the gel turns colour when pressure is applied.

Figure 4:
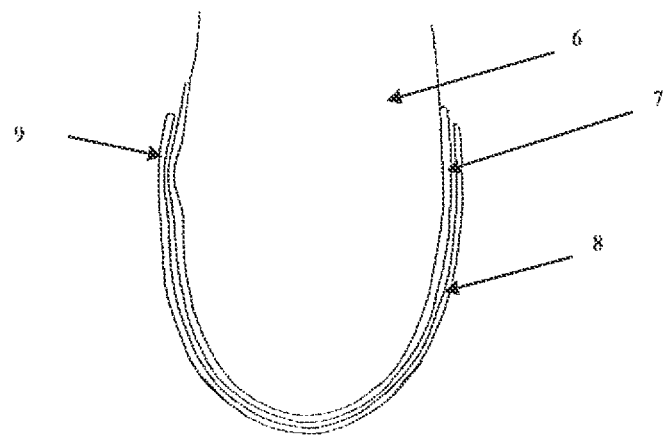
FIG. 4 is a cross sectional drawing of a residual limb with the FIG. 3 liner shown installed in a socket. A high pressure area is indicated.

FIG. 4—In the second embodiment the liner is made of one layer of gel or other suitable material. When the residual limb (6) is inserted into the liner (7), which is then inserted into the transparent or translucent socket (8), the pressure on the liner causes a change in colour indicating the area of high pressure (9) while the patient is wearing the device.

Figure 5:
FIG. 5 is a cross sectional drawing of a single-layered liner made of a material that becomes more transparent and allows an underlying material or object to appear more clearly through the outer layer when viewed from outside of the liner.

FIG. 5—The third embodiment is a flexible sheet-like material fabricated out of an elastomeric gel such a silicone, urethane, thermoplastic elastomer, or other suitable material. The gel is pigmented and fabricated in such a way that the gel becomes more transparent when pressure is applied so as to allow an underlying material to show through, indicating the high pressure area.

Figure 6:
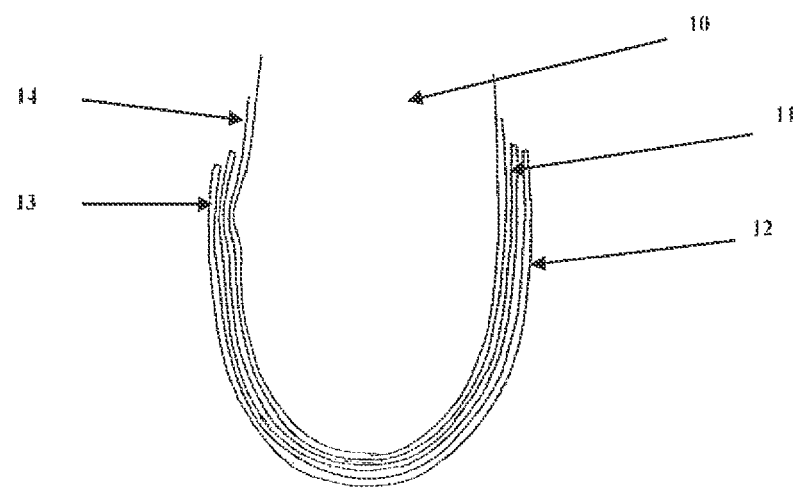
FIG. 6 is a cross sectional drawing a residual limb with the FIG. 5 liner shown installed in a socket with coloured sock in between the skin and the liner. A high pressure area is indicated.

FIG. 6—In the third embodiment the liner is made of one layer of gel or other suitable material. When the residual limb (10) is inserted into the liner (11), which is then inserted into the transparent or translucent socket (12), the liner thins out in the high pressure spot (13) allowing an underlying material (14) to show through the liner. This indicates the location of the high pressure spot.

The method and the result of the method is the use of the liner as a pressure assessment tool and a fitting tool for constructing and adjusting a prosthetic socket, orthopaedic device, or for any application requiring analysis of body pressure against an object.

Although the present invention has been described with reference to preferred embodiments, workers skilled in the art will recognize that changes may be made in form and detail without departing from the spirit and scope of the invention.

The invention claimed is:

1. A sheet material, contoured sheet material, or interface liner formulated and fabricated such that when pressure is applied to said sheet material, contoured sheet material, or interface liner, said sheet material, contoured sheet material, or interface liner indicates a spot at which the pressure has been applied by effecting a change in a color or appearance of said sheet material, contoured sheet material, or interface liner, comprising:
   at least a first layer that is partially translucent; and
   a second layer that has a color, wherein the first layer thins out under pressure so that the visibility of the color of the second layer through the first layer is changed.

2. The sheet material, contoured sheet material, or interface liner of claim 1, wherein the first layer has a color that is different from, in particular lighter than, the color of the second layer.

3. The sheet material, contoured sheet material, or interface liner of claim 1, wherein at least one of the first layer and the second layer consist of urethane, elastomer, silicon, polyurethane, thermoplastic elastomer, gel or other appropriate material.

4. The sheet material, contoured sheet material, or interface liner of claim 1, wherein said sheet material, contoured sheet material, or interface liner is used to fabricate a prosthetic interface liner configured for use with a prosthetic device.

5. The sheet material, contoured sheet material, or interface liner of claim 1, wherein said sheet material, contoured sheet material, or interface liner is configured for use with an application requiring dynamic analysis of body pressure against an object.

6. The sheet material, contoured sheet material, or interface liner of claim 1, wherein said sheet material, contoured sheet material or interface liner is configured for use with an application requiring dynamic analysis of pressure between surfaces of two objects.

7. The sheet material, contoured sheet material or interface liner of claim 1, wherein the first layer has a thickness of 0.5 mm to 1.5 mm.

8. The sheet material, contoured sheet material, or interface liner of claim 1, wherein the first layer and the second layer have different durometer or harnesses.

9. The sheet material, contoured sheet material, or interface liner of claim 8, wherein the second layer has a greater durometer or hardness than the first layer.

10. The sheet material, contoured sheet material or interface liner of claim 3, wherein at least one of the first layer and the second layer comprises silicone having a shore hardness of 30 to 35 shore 00.

11. The sheet material, contoured sheet material, or interface liner of claim 1, wherein the first later thins out due to compression or displacement of a material of the first layer.

12. The sheet material, contoured sheet material, or interface liner of claim 3, wherein at least one of the first and second layers comprises a viscoelastic material or a material that flows upon application of pressure.

13. A method for determining pressure distribution of a pressure that is applied to a residual amputation limb by an orthopedic appliance, wherein the method comprises the following steps:
- arranging a sheet material, contoured sheet material, or interface liner on the residual amputation limb; and
- positioning the residual amputation limb with the sheet material, contoured sheet material or interface liner in a transparent molding.

14. The method of claim 13, further comprising applying a lubricant prior to positioning of the residual amputation limb in the molding in order to reduce a sliding resistance between the sheet material, contoured sheet or interface liner and the molding.

15. The method of claim 13, wherein the molding is a prosthesis socket.

* * * * *